United States Patent [19]

Eibl et al.

[11] Patent Number: 4,886,758
[45] Date of Patent: Dec. 12, 1989

[54] METHOD OF DETERMINING INCOMPATIBILITY-REACTION-CAUSING SUBSTANCES IN BLOOD PRODUCTS AS WELL AS A METHOD OF INACTIVATING SAID INCOMPATIBILITY-REACTION-CAUSING SUBSTANCES

[75] Inventors: Johann Eibl; Yendra Linnau; Otto Schwarz, all of Vienna, Austria

[73] Assignee: Immuno Aktiengesellschaft fur Chemisch-Medizinische Produkte, Vienna, Austria

[21] Appl. No.: 907,652

[22] Filed: Sep. 15, 1986

Related U.S. Application Data

[63] Continuation-in-part of Ser. No. 584,933, Feb. 29, 1984, abandoned, and a continuation of Ser. No. 886,724, Jul. 18, 1986, abandoned.

[30] Foreign Application Priority Data

Mar. 16, 1983 [AT] Austria ................................... 931/83

[51] Int. Cl.[4] .......................... C07K 3/00; C07K 15/00; A61K 39/395
[52] U.S. Cl. .................................... 435/269; 435/68.1; 435/272; 530/386; 530/387; 424/85.8
[58] Field of Search .................... 424/85, 85.8; 435/68, 435/69, 387, 269, 272; 530/386, 387

[56] References Cited

U.S. PATENT DOCUMENTS

4,276,283  1/1981  Eibl et al. ............................... 424/86
4,371,612  2/1983  Matsumoto et al. ................... 435/47

FOREIGN PATENT DOCUMENTS

56-7721   1/1981  Japan .
56-15215  2/1981  Japan .

*Primary Examiner*—Blondel Hazel
*Attorney, Agent, or Firm*—Burns, Doane, Swecker & Mathis

[57] ABSTRACT

There is disclosed a method of determining the presence of incompatibility-reaction-causing substances in blood products. There is also disclosed a method of inactivating incompatibility-reaction-causing substances in blood products to be applied therapeutically and prophylactically. For this purpose, a fraction obtained from human or animal blood is treated with pancreas enzymes bound to water insoluble carrier material and, optionally, the fraction is subjected to further fractionation and concentration.

4 Claims, 3 Drawing Sheets

METHOD OF DETERMINING INCOMPATIBILITY-REACTION-CAUSING SUBSTANCES IN BLOOD PRODUCTS AS WELL AS A METHOD OF INACTIVATING SAID INCOMPATIBILITY-REACTION-CAUSING SUBSTANCES

CROSS REFERENCE TO RELATED APPLICATIONS

The subject application is a continuation-in-part of U.S. Ser. No. 584,933, filed Feb. 29, 1984 now abandoned, and a continuation of U.S. Ser. No. 886,724, filed July 18, 1986 now abandoned.

BACKGROUND OF THE INVENTION

The invention relates to a method of determining incompatibility-reaction-causing substances in therapeutically and prophylactically applicable blood products as well as use of this method for testing the safety of these products.

The invention further relates to a method of inactivating incompatibility-reaction-causing substances in therapeutically or prophylactically applicable immunoglobulin-containing blood fractions while using proteolytically active enzymes. In particular, the invention relates to a method of inactivating such substances at the production of new immunoglobulin-G-containing fractions from human or animal plasma suited for intravenous applications.

Immunoglobulin-containing preparations may be applied in case of primary and secondary immune defects, A-gamma-globulinemia or hypogammaglobulinemia, antibody deficiency syndrome, virus infections or bacterial infections.

For obtaining immunoglobulin-containing preparations from human or animal plasma, various methods are already known, e.g. the precipitation with ethanol (J. L. Oncley, M. Melin, D. A. Richart, J. W. Cameron and P. M. Gross, J. Am. Chem. Soc. 71, 541 (1949)) as well as modified ethanol methods according to H. F. Deutsch, L. F. Gosting, R. A. Alberty and J. W. Williams, J. Biol. Chem. 164, 109 (1946) as well as P. Kistler and H. Nitschmann, Vox Sanguinis 7, 414 (1962).

Furthermore, a method is known according to which immunoglobulin is precipitated from plasma by means of ammonium sulfate and polyethyleneglycol (A. Polson, G. M. Potgieter, J. F. Largrier, G. E. F. Mears and F. J. Jourbet, Biochim. Biophys. Acta. 82, 463 (1964)). According to other methods, the use of ion exchangers has been suggested (E. A. Peterson and H. A. Sober, J. Am. Chem. Soc. 78, 741 (1956)).

These methods had the disadvantage that the obtained preparations were suited for intramuscular application only. With intravenous application, they exhibited undesired side reactions, such as vasoactive effects.

Therefore, efforts have been made to reduce side reactions or side effects, to which end immunoglobulin-containing preparation were treated with soluble proteolytic enzymes, such as pepsin, plasmin, papain and others (German Pat. No. 1,148,037, as well as Swiss Pat. No. 392,780). However, by this treatment the molecular structure of the immunoglobulins is changed, which may result in a shortened biologic half-life period or in undesired side effects, such as vasoactive or leucopenic activity. It was also found that enzyme residues remain in the preparations, thereby contaminating the same. The storability is accordingly low, the danger of a progressing proteolytic cleavage is great.

German Offenlegungsschrift No. 28 46 412 describes a method of producing immunoglobulins immunologically modified in their Fc-portion, wherein the immunoglobulin-containing fraction is treated with a protease solution. These products are said to have an antiallergic effect in local or systemic application. The method is unsuited for the production of an intravenously applicable preparation, as the protease solution is not or not completely removable from the product and continues with its decomposing effect.

In German Offenlegungsschrift No. 29 36 047 a method for the production of an intravenously administrable immunoglobulin preparation is described, in which a combined purification with ammonium sulfate and polyethyleneglycol is carried out in the presence of a soluble carbohydrate or of a polyol. It is true that vasoactive side effects have been eliminated, yet an improvement in terms of safety and reproducibility in case of intravenous application is still desirable.

Among the prior art, also the Japanese patent applications published under Nos. 56-7721 and 56-15215 as well as German Offenlegungsschrift No. 32 20 309 are to be mentioned, which have as their objects methods for the production of intravenously applicable immunoglobulin preparations. The treatment is to be effected with immobilized plasmin or immobilized pepsin, yet the results attainable thereby are not satisfactory, either, because the preparations have an undesirably high anticomplementary activity.

SUMMARY OF THE INVENTION

The invention aims at avoiding the disadvantages and difficulties described and has as its object to provide a method with which substances that cause incompatibility reactions are reliably eliminated and an extensive safety of the preparations to be applied therapeutically or prophylactically is ensured.

The object is achieved according to the invention in that a fraction obtained from human or animal blood is treated with pancreas enzymes bound to water insoluble carrier material, such as trypsin or chymotrypsin or pancreas protease, and the treated fraction, if desired, is subjected to further fractionation and concentration.

Advantageously, Sepharose 4 B gel is used as the water insoluble carrier material.

The immunoglobulin-containing fraction treated with enzymes bound to water insoluble carrier material may be further purified by protein precipitating agents and processed into a final product.

DETAILED DESCRIPTION OF THE EMBODIMENTS

Figure 1:
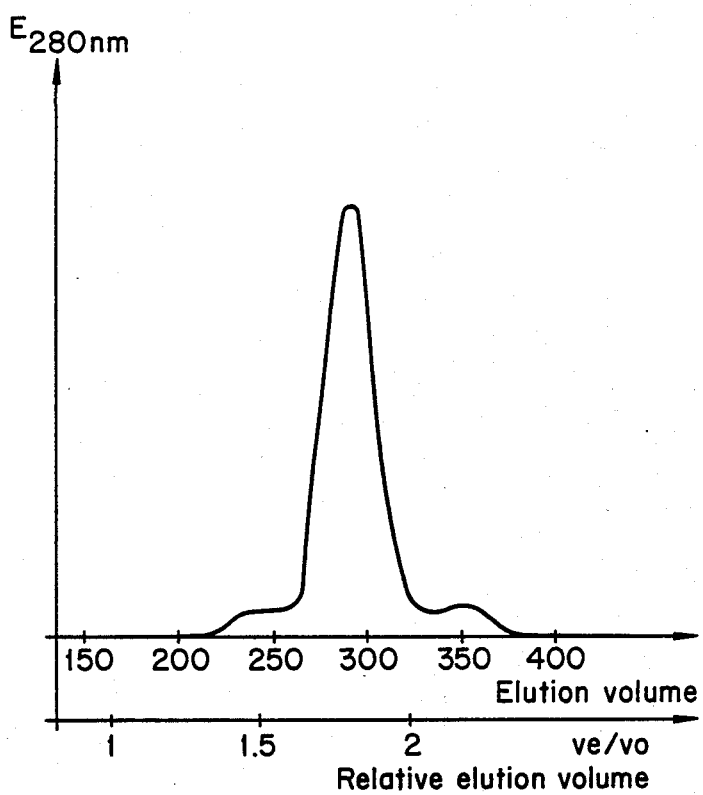
FIG. 1 is an elution curve indicating the protein contents of individual fractions measured as an extinction of 280 nm.
Figure 2:
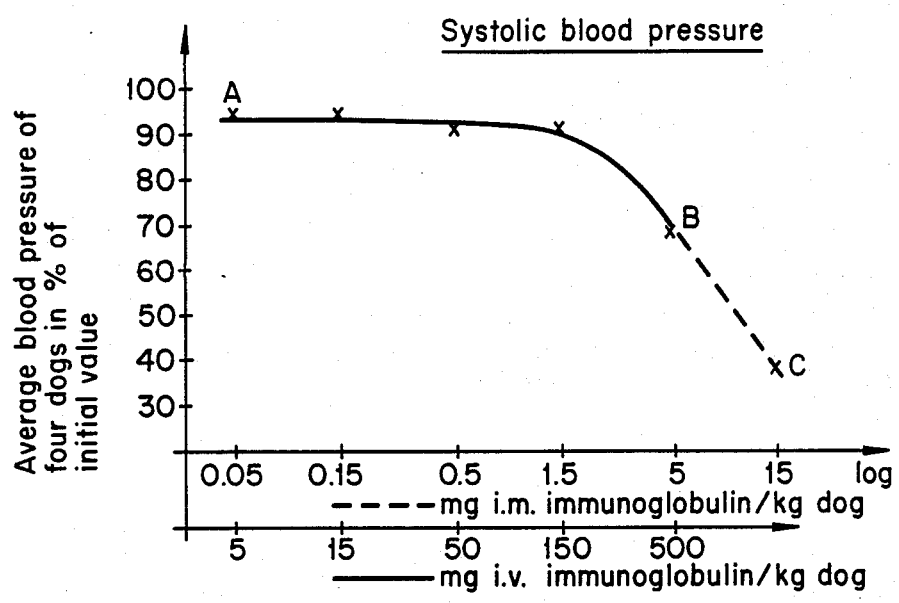
FIGS. 2 and 3 are, respectively, blood pressure curves with systolic and diastolic measurements for four dogs as a function of administered amounts in mg/kg.
Figure 3:
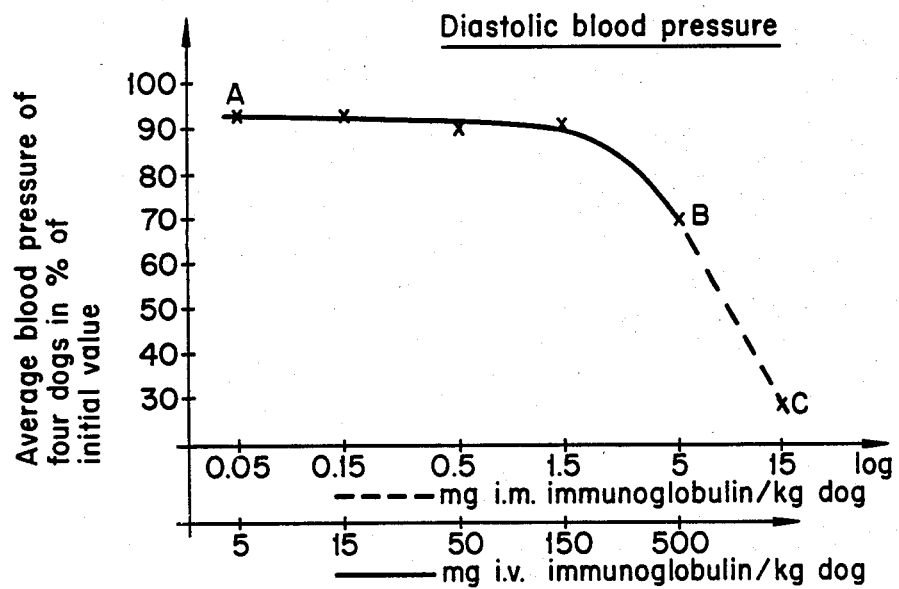
Figure 4:
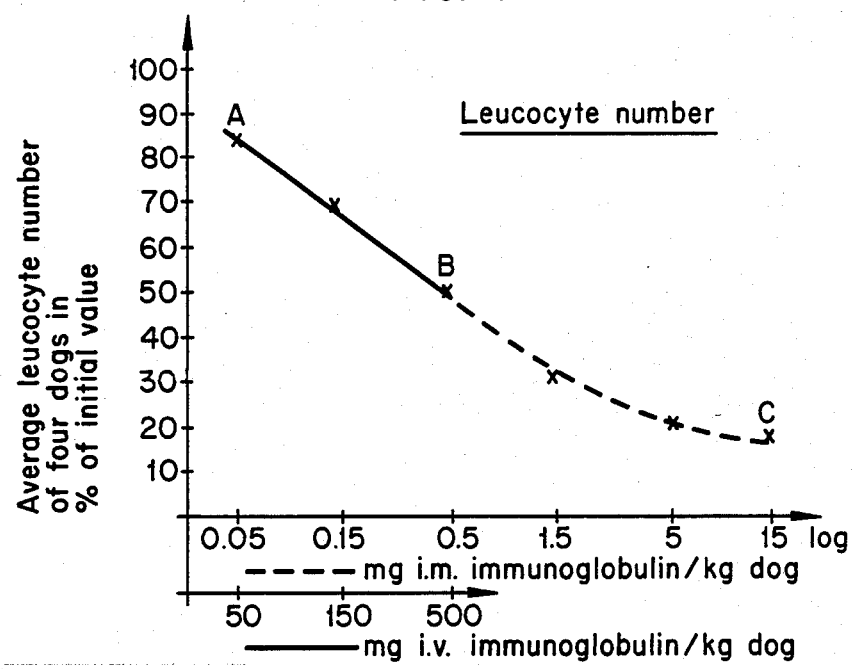
FIG. 4 is a curve indicating the leucopenic effect in the dog test as an average of four animals.
Figure 5:
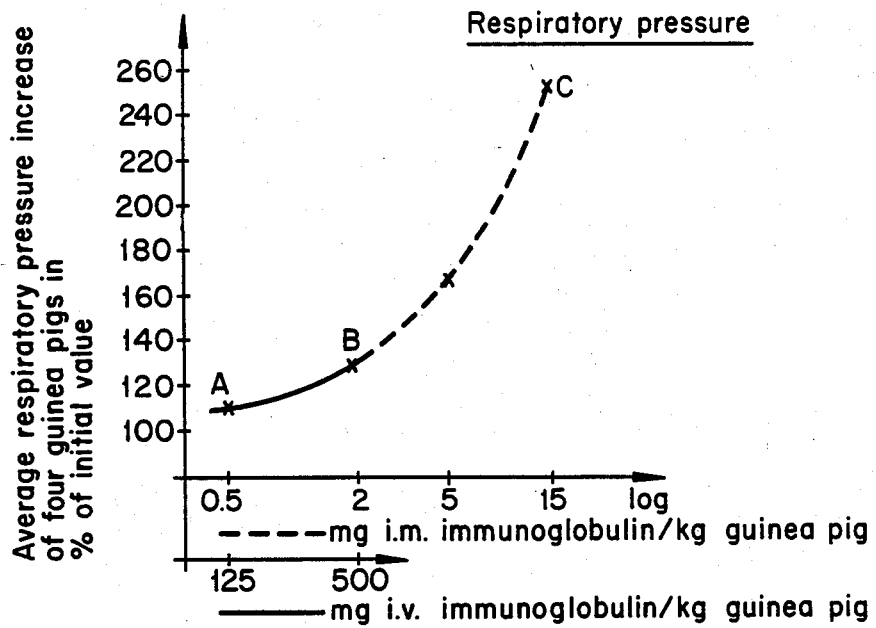
FIG. 5 is a curve indicating the bronchospastic effects in the guinea pig test.

In particular, a combination of the following purification and concentration measures has proved successful:
treating human or animal plasma with ethanol at a temperature of below 0° C. to obtain an immunoglobulin-containing precipitate,
removing ethanol from said immunoglobulin-containing precipitate by dialysis or by diafiltration or by freeze-drying to obtain an immunoglobulin-containing fraction;
treating the immunoglobulin-containing fraction with an immobilized enzyme from the group of trypsin, chymotrypsin or pancreas protease at an elevated temperature of about 37° C.;
precipitating from the thus treated fraction purified immunoglobulin substantially comprised of IgG by means of a protein precipitating agent, preferably polyethyleneglycol, and
dissolving the precipitate, sterile filtering the solution and finally lyophilizing.

An analysis of the molecular structure of the fractions prepared according to the invention reveals, as a new characteristic feature, a composition of at least 90% monomer IgG molecules and at least 90% functionally intact IgG molecules.

The determination of the monomer IgG molecules is effected by gel permeation chromatography (gel filtration) according to H. Determann, "Gel-Chromatographie", Springer Verlag, Berlin, 1967, in the following manner:

The molecules are separated according to their molecular weight. Molecules that are larger than the largest pores in the swollen gel cannot penetrate into the gel and are eluted first (the corresponding elution volume being $V_o$). Smaller molecules penetrate into the gel pores and hence migrate more slowly (the corresponding elution volume being $V_e$). Thus, the elution volume ($V_e$) is a characteristic parameter of a substance. The relative elution volume $V_e/V_o$ of a substance is independent of the geometric column dimensions and the column. The determination is carried out, e.g., by filling a separation column of 2.6 cm diameter and 100 cm length with a gel, e.g., agarose polyacrylamide (tradename Ultrogel AcA 34), that has been swollen in a sodiumphosphate-sodiumchloride buffer (PBS), pH 7.0 50 mg of an immunoglobulin preparation are applied onto the column and eluted with sodiumphosphate-sodiumchloride buffer, pH 7.0, at a flow rate of 20 ml/h.

The eluates are collected in 4.5 ml fractions and the elution curve is detected at 280 nm by means of a UV detector. On account of the elution diagram, the individual components are pooled and the elution volume as well as the protein concentration are determined.

The immunoglobulins that have a relative elution volume $V_e/V_o$ between 1.30 and 2.20 are denoted as monomer IgG molecules and, according to the invention, amount to at least 90% of the total protein. In this connection, it is noted that the IgG molecules that have a $V_e/V_o$ of 1.30 to 1.65 are denoted as dimer IgGs; however, since they are in a reversible equilibrium with the monomer IgG molecule having a $V_e/V_o$ of 1.66 to 2.20, they are to be considered as monomers (cf. J. S. Finlayson, B. L. Armstrong and A. M. Young, Acta Radiologica Supplementum 310, (1971), 114).

The determination of the functionally intact IgG molecules is carried out according to an affinity chromatography method with protein A Sepharose (FEBS Letters, Vol. 28, 1972, 73 et seq.; H. Hjelm, K. Hjelm, J. Sjoquist, "Protein A from Staphylococcus aureus, its Solution by Affinity Chromatography and its Use as an Immunosorbent for Isolation of Immunoglobulins"). This method is based on the fact that protein A from staphylococcus aureus gets into interaction with the IgG molecules from subgroups IgG 1, 2 and 4, binding the same. The functionally active positions are the $C_H2$ and $C_H3$ regions, which are parts of the H-chain of the IgG molecules.

The pooled fractions $V_e/V_o$ of 1.30 to 2.20 from the molecular weight determination by means of gel filtration are adjusted to a certain protein concentration, 10 mg protein of this preparation being chromatographed over 10 ml protein A Sepharose, immobilized protein A. The bound IgGs 1,2 and 4 are eluted with a sodiumcitrate-citric acid buffer, pH 3.0. Then the bound and the unbound IgGs are calculated.

According to a preferred embodiment, the fraction according to the invention has such a low anticomplementary activity that it requires no less than 40 mg protein to neutralize one CH50 unit.

The determination of this characteristic feature is realized according to "Public Health Monograph" No. 74; Standardized Diagnostic Complement Fixation Method and Adaptation to Microtest, Washington, 1965, and E. A. Kabat and M. Mayer, Experimental Immunochemistry; 2nd Ed. Thomas Springfield 1961.

By electrophoretic determination, at least 95% of gammaglobulin is detected in the fractions according to the invention. The determination is effected according to Michael D. Gebott, Beckman Microzone Electrophoresis Manual, Beckman Instruments, Inc. 1977, 015-083630-C.

Since the treating physician has at his disposal immunoglobulin-containing preparations that contain greater or lesser amounts of incompatability-reaction-causing substances, it is the object of the present invention to have at hand a safe determination method, by which the pharmacological properties of the preparations can be determined in a simple and rapid manner. In particular, these preparations should be essentially free from vasoactive substances, leucopenic substances and bronchospastic substances. Moreover, it would be advantageous to have pharmacologically permissible limit values (maximum values) for testing the safety of the immunoglobulin-containing preparations prior to their administration to humans.

In accordance with the invention, this object is achieved in one of three possible ways. The blood products are intraarterially injected in dogs and the decrease in blood pressure is determined, or the blood products are intraarterially injected in dogs and the decrease in the number of leucocytes is determined, or the blood products are intraarterially injected in guinea pigs and the increase in respiratory pressure is determined.

Advantageously, immunoglobulin-containing blood products are used for determination.

The indicated methods are based on the finding that with the intraarterial injection of the preparation in dogs or guinea pigs the side-effect-causing substances demonstrate effects which are about ten times as strong as with intravenous application in man. Thus, in this manner, the innocuous limit values (maximum values) for permissible impurities in preparations to be intravenously applied in humans can be defined.

The indicated methods of determination are advantageously used for testing the safety of immunoglobulin-containing preparations. The limits are set such that for a sufficient safety with maximum possible dose a significant decrease in blood pressure in the dog test and/or a significant decrease in the number of leucocytes in the dog test and/or a significant increase in the respirator pressure in the guinea pig test are not detectable.

As regards the testing of immunoglobulin-containing preparations with a view to their vasoactive effect, it has been found that sufficient safety is present whenever with a dose of more than 500 mg/kg body weight a decrease in blood pressure of at most 30% is detectable as an average of four animals.

As regards the testing of immunoglobulin-containing preparations with a view to their leucopenic effect, it has been found that sufficient safety is present whenever with a dose of more than 500 mg/kg body weight a decrease in the number of leucocytes of at most 50% is detectable as an average of four animals.

As regards the testing of immunoglobulin-containing preparations with a view to their bronchospastic effect, it has been found that sufficient safety is present whenever with a dose of more than 500 mg/kg body weight an increase in respiratory pressure of at most 30% is detectable as an average of four animals.

Between the above indicated limit values and the number of test animals there is an interrelationship insofar as, when the number of test animals is increased, the tolerable limit value can be lowered and vice versa; which is to say that with fewer test animals the safety limit should be raised.

The vasoactive effect is determined in the following manner:

In test animals (hybrids of both sexes) the vena jugularis and the arteria carotis are dissected upon narcotization. Before anesthesia, a fasting time of at least 12 hours is fixed. Per test substance four qualified dogs are required, i.e. such dogs which, upon intraarterial application of standardized intramuscularly applicable immunoglobulin ("standard substance") exhibit a vasoactive effect (blood pressure decrease) of at least 30% at a dosage of 50 mg/kg body weight. This standardized intramuscularly applicable immunoglobulin is prepared according to the initially mentioned method by J. L. Oncley, M. Melin, D. A. Richart, J. W. Cameron and P. M. Gross, J. Am. Chem. Soc. 71, 541 (1949). Dogs which do not show any reaction to the standard substance cannot be used for comparative tests.

From the standard substance, 160 mg are dissolved in 1 ml aqua ad injectabilia and diluted to 16.7 mg/ml with isotonic NaCl solution. The dissolved material is used within four hours.

The intravenously applicable immunoglobulin G according to the invention is dissolved with aqua ad injectabilia such that 1 ml contains 165 mg protein. The dissolved material is used within four hours.

The animals are anesthesized with an intravenous single dose of 40 mg/kg Nembutal (barbiturate), and the vena jugularis externa, after division, is dissected on the lower rim of the mandible, a catheter being bound in. Thereupon, the arteria carotis is laid bare from the same skin incision and a catheter is bound in. After dissection of the arteria a waiting period of approximately 30 minutes is accomplished in order to gain stable initial values. By means of a pressure transducer, the central venous pressure is measured via the deep venous catheter and the arterial blood pressure is measured via the shallow arterial catheter. Via the arterial catheter, at first the immunoglobulin G i.v. applicable according to the invention and then the standard substance are injected.

During the whole time the experiment is being carried out the systolic and the diastolic blood pressures are recorded via the arterial catheter by means of a pressure transducer.

The blood pressure mean value (systolic and diastolic) as well as the mean value of the number of leucocytes prior to injection of the test substance and the standard substance are determined. The maximum blood pressure decrease is determined by measuring the blood pressure over 20 min after injection of the test substances.

The vasoactive effect of the tested i.v. applicable immunoglobulin G according to the invention is established by injecting 500 mg/kg body weight of dog and comparing the average systolic and diastolic blood pressure decreases in per cent in four dogs with the blood pressure decreasing effect of the i.m. applicable standard substance.

The determination of the leucopenic activity is carried out in the following manner:

In test animals (hybrid dogs of both sexes) the vena jugularis and the arteria carotis are dissected upon narcotization. Before anesthesia, a fasting time of at least 12 hours is fixed. Per test substance four qualified dogs are required, which, upon intraarterial application of standardized intramuscularly applicable immunoglobulin (standard substance) exhibit a leucopenic effect (leucocyte decrease) of at least 50% at a dosage of 50 mg/kg body weight. Dogs which do not show any reaction to the standard substance cannot be used for comparative tests.

The preparation of the test animals and test substances is effected in the same way as described above.

To investigate the leucocyte number, blood samples are drawn. For the first blood sample, 40 $\mu$l blood are admixed with 20 ml Isotone II (COULTER) and measured in the Coulter counter. Subsequently, further blood samples are drawn after 10, 15, 16, 17, 18 and 19 min to determine the number of leucocytes. Then 500 mg immunoglobulin G are immediately injected intraarterially within 90 s. Further blood samples are drawn 1, 2, 3, 4, 5, 7, 10, 15 and 20 min after injection.

After 20 min 50 mg immunoglobulin/kg body weight of the standard substance are injected within 90 s. Blood samples are again drawn after 1, 2, 3, 4, 5, 7, 10, 15 and 20 min.

The maximum decrease in the leucocyte number is determined by assessment of the blood samples drawn 1, 2, 3, 4, 5, 7, 10, 15 and 20 min after injection of the sample.

The leucopenic effect of the tested i.v. applicable immunoglobulin G is determined by injection 500 mg/kg body weight of dog and comparing the average leucocyte decrease in per cent in four dogs with the leucopenic effect of the i.m. applicable standard substance.

The determination of the bronchospastic (respiratory pressure increasing) effect in guinea pigs is effected in the following manner:

In test animals (male guinea pigs) the trachea is dissected in the region of the larynx upon narcotization. After incubation the test animal is respirated by means of a respirator at a respiratory volume corresponding to the body weight of the animal and at a respiration frequency of 80/min. Thereafter, the arteria carotis is dissected bare from the same skin incision. Upon intraarterial injection of the test substance, the respiratory pressure is continuously measured.

For the test, laboratory-bred guinea pigs of the male sex having a body weight of between 500 and 700 g are used. Per test substance four qualified guinea pigs are required, which, upon intraarterial application of standardized i.m. applicable immunoglobulin (standard substance) exhibit an increase in the respiratory pressure by at least 30% at a dosage of 50 mg/kg body weight. Guinea pigs which do not show any reaction to the standard substance cannot be used for comparative tests.

From the standard substance, 160 mg are dissolved in 1 ml aqua ad injectabilia and diluted to 16.7 mg/ml with isotonic NaCl solution. The dissolved material is used within four hours.

The i.v. applicable immunoglobulin G according to the invention is dissolved with aqua ad injectabilia such that 1 ml contains 165 mg protein. The dissolved material is used within four hours.

The animals are narcotized; then the trachea is dissected in the region of the larynx, a tracheal cannula being bound in. By means of a respirator, the test animal is respirated at a respiratory volume corresponding to the body weight and at a respiration frequency of 80/min. A Harvard pump type 681 is used as respirator.

Thereupon, the arteria carotis is dissected bare from the same skin incision, a catheter being bound in. The registration of the respiratory pressure is effected via a pressure transducer connected to the respiration tube by a T-piece.

After dissection it is waited for at least 10 min in order to gain stable initial values. Thereafter, the zero point is determined and after an additional two to three minutes 150 mg immunoglobulin/kg body weight of i.v. applicable immunoglobulin G are intraarterially injected within 90 s via the catheter.

After 20 min, 50 mg standard substance/kg body weight are intraarterially injected within 90 s.

The maximum increase in the respiratory pressure during the 20 min following upon the injection of the sample is determined and compared to the initial mean value.

The bronchospastic effect of the tested i.v. applicable immunoglobulin G is determined by injecting 500 mg/kg body weight of guinea pig intraarterially and comparing the average respiratory pressure in per cent of four guinea pigs with the respiratory pressure increasing effect of i.m. applicable immunoglobulin G, standard substance.

The methods according to the invention will be explained in more detail by the following working instructions and examples.

Working instructions for the preparation of an immobilized enzyme.

The production of an immunoglobulin fraction containing only small amounts of incompatibility-reaction-causing substances is illustrated.

Working Instruction 1

1 l Sepharose 4 B-Gel (Pharmacia), after washing in 4 l of distilled water, is mixed with 200 g bromocyan dissolved in 100 ml acetonitrile at a pH of 11.0. The reaction mixture is cooled by an icebath. After removal of the liquid phase, the gel is mixed with 800 mg trypsin (Sigma) dissolved in 1 l 0.2 molar NaHCO3. The trypsin that has not bound is separated by filtration from the trypsin that has bound to the gel.

After mixing the immobilized trypsin with 1 l of a 1 molar glycine solution, it is thoroughly washed free of proteins by a 0.2 molar NaHCO3 solution. Finally, the gel (immobilized) trypsin is suspended in 1 l 0.9% NaCL solution - it is ready for use for incubation with an immunoglobulin fraction.

Working Instruction 2

The insoluble enzyme is prepared in the same manner as in Working Instruction 1, instead of trypsin, pancreas protease (Merck) is used.

Working Instruction 3

Working Instruction 1 is repeated, instead of trypsin, alpha-chymotrypsin (Sigma) is used.

Examples for the preparation of the immunoglobulin-G-containing fraction.

EXAMPLE 1

Human blood plasma is mixed with 8% ethanol at a pH of 7.2 and a temperature of $-2°$ C. After separation of the precipitate, the ethanol concentration is increased to 25% and the temperature is lowered to $-6°$ C. simultaneously. The precipitate, which contains immunoglobulin, is further purified by extraction with a phosphate acetate buffer and is mixed with 12% ethanol at a pH of 5.4 and a temperature of $-2°$ C.

The precipitate (containing alpha- and beta-globulin) is discarded. The ethanol concentration of the supernatant is increased to 25% at a pH of 7.2 and a temperature of $-10°$ C. The precipitated paste-like immunoglobulin is collected and the ethanol is removed by dialysis.

Thereafter, 170 g/l of ammonium sulfate are added to the dialysate at a pH of 6.25, the precipitate is separated and discarded. Further ammonium sulfate is added to the supernatant at a pH of 7.2 up to a concentration of 280 g/l. The precipitate is dissolved in water and dialyzed to remove the ammonium sulfate.

After dialysis the ionic strength of the immunoglobulin solution is adjusted to 0.15.

100 g immunoglobulin are prepared with 30 ml trypsin immobilized according to Working Instruction 1 and treated for 72 hours at $37°$ C. After removal of the gel (immobilized) trypsin, the treated immunoglobulin is precipitated by 135 g/l of polyethyleneglycol 4000. The precipitate is dissolved in 0.9% NaCl, sterile filtered, filled in containers and rendered storable by lyophilization.

EXAMPLE 2

The recovery of the immunoglobulin-containing fraction takes place in the same manner as in Example 1.

Incubation is effected by the immobilized pancreas protease prepared according to Working Instruction 2. 100 g immunoglobulin are treated with 70 ml gelantinous immobilized pancreas protease and maintained at $37°$ C. for 70 hours. After removal of the gel, the supernatant is admixed with 75 g/l polyethyleneglycol 4000 and the precipitate containing impurities is discarded.

Further polyethyleneglycol 4000 is added to the supernatant up to a final concentration of 85 g/l. The precipitate formed as discarded.

By increasing the polyethyleneglycol concentration to 135 g/l, the purified immunoglobulin is precipitated and rendered storable as in Example 1.

EXAMPLE 3

The recovery of the immunoglobulin-G-containing fraction is realized in the same manner as in Example 1, yet the treatment with immobilized alpha-chymotrypsin at 37° C. is carried out for 72 hours.

The data of the immunoglobulin-G-containing fractions of the invention prepared according to Examples 1 to 3, i.e., the contents of monomer IgG molecules, the contents of functionally intact IgG molecules, the anticomplementary activity as well as the content of gammaglobulin at the electrophoretic separation were determined as described below. These values are illustrated in the following Tables as well as in the annexed FIG. I.

FIG. I illustrates an elution curve under the indicated conditions between 150 and 400 ml as well as the relative elution volume $V_e/V_o$. The curve indicates the protein contents of the individual fractions, measured at an extinction of 280 nm.

In the following Table 1, the $V_e/V_o$ ratio according to the gel permeation chromatography carried out for the individual regions covered by the curve are indicated. As will be apparent, the $V_e/V_o$ ratio in the region of 1.30 to 2.20 is more than 90%.

TABLE 1

| | Gel permeation chromatography $V_e/V_o$ | | |
|---|---|---|---|
| | 1.0–1.29 | 1.30–2.20 | 2.21–2.70 |
| Example 1 | traces | 92.4% | 7.6% |
| Example 2 | — | 93.2% | 6.8% |
| Example 3 | — | 91.8% | 8.2% |

In Table 2 the ratio of the IgG molecules bound to protein A and the unbound IgG molecules is illustrated, the bound molecules corresponding to the functionally intact ones. As is apparent, the content of functionally intact IgG molecules in the total fraction is more than 90%.

TABLE 2

| | Affinity chromatography with protein A—Sepharose | | |
|---|---|---|---|
| | % of fraction $V_e/V_o$ 1.30–2.30 | | % of total immunoglobulin-G-containing fraction |
| | unbound | bound | |
| Example 1 | 1.5 | 98.5 | 91.0 |
| Example 2 | 0.9 | 99.1 | 92.3 |
| Example 3 | 1.2 | 98.8 | 90.7 |

In Table 3 the values for the anticomplementary activity and the electrophoresis are indicated, from which it can be seen that, with the preparations of all Examples, values for the anticomplementary activity of more than 50 mg immunoglobulin-G-containing fraction were required to neutralize a C'H-50 unit and electrophoretically determined values of pure gammaglobulin of more than 97% were obtained.

TABLE 3

| | Anticomplementary activity | Electrophoresis |
|---|---|---|
| Example 1 | >50 mg/C'H—50 | >97.0% pure gammaglobulin |
| Example 2 | >50 mg/C'H—50 | >97.0% pure gammaglobulin |
| Example 3 | >50 mg/C'H—50 | >97.0% pure gammaglobulin |

The pharmacologic characteristics and data of the immunoglobulin-G-containing fractions of the invention prepared according to Examples 1 to 3, i.e. the vasoactive and the leucopenic effects in dog test and the bronchospastic effect in guinea pig test, were determined as described above; these values are obvious from the following Tables.

TABLE 4

Average blood pressure of four dogs in % of initial value after injection of 500 mg of the preparation according to invention per kg body weight

| | Systolic blood pressure | Diastolic blood pressure |
|---|---|---|
| Preparation according to Example 1 | 91% | 86% |
| Preparation according to Example 2 | 93% | 89% |
| Preparation according to Example 3 | 81% | 79% |

TABLE 5

Average leucocyte number of four dogs in % of initial value after injection of 500 mg of the preparation according to invention per kg body weight

| Example 1 | 73% |
|---|---|
| Example 2 | 62% |
| Example 3 | 52% |

TABLE 6

Average respiratory pressure increase of four guinea pigs in % of initial value after injection of 500 mg of the preparation according to invention per kg body weight

| Example 1 | 102% |
|---|---|
| Example 2 | 110% |
| Example 3 | 125% |

The superiority of the intravenously applicable immunoglobulin-G-containing fractions to the known intramuscularly applicable ones will become clearly apparent from the annexed FIGS. II to IV.

In Diagram II the blood pressure curves with the systolic and diastolic measurements in four dogs each are entered, the administered amounts in mg/kg body weight of the animals each being plotted on the abscissa. The full line in the region from A to B corresponds to the course of the blood pressure upon administration of the intravenously applicable immunoglobulin-G-containing preparations according to the invention; the course of the curve from A to C (full line and broken line) corresponds to the course of the blood pressure curve upon application of the i.m. standard substance. It is evident that upon application of the i.m. applicable standard substance at 5 mg/kg body weight the blood pressure has decreased by 30%, while upon application of the preparation according to the invention this decrease has occurred only at a dosage of 500 mg/kg body weight, i.e. the intravenously applicable immunoglobulin of the invention has a vasoactive effect that is at least 100 times less than that of known i.m. applicable preparations, under otherwise equal conditions.

From FIG. III the leucopenic effect in the dog test as an average of four animals is apparent as a comparison between the i.v. applicable preparations of the invention and the standardized i.m. applicable standard preparation. The full line in the region from A to B reflects the intravenously applicable immunoglobulin-G-containing preparation and the line from A to C (full line and broken line) indicates the course of the leucocyte number curve upon application of the i.m. applicable standard substance. It is apparent that upon application of the i.m. applicable standard substance the leucocytes have decreased by 50%, while upon application of the preparation according to the invention this decrease has occurred only at a dosage of 500 mg/kg body weight, i.e. the intravenously applicable immunoglobulin-G-containing preparation has a leucopenic effect that is at least 1,000 times less than that of known i.m. applicable preparations, under otherwise equal conditions.

A comparison of the bronchospastic effects in the guinea pig test according to FIG. IV looks similar, the course of the curve from A to B (full line) corresponding to the i.v. applicable preparation of the invention and the course of the curve from A to C (full line and broken line) corresponding to the standardized i.m. applicable preparation. The 30% increase in the respiratory pressure, with a known i.m. applicable preparation, occurs already at a dosage of 2 mg/kg body weight, while the same increase is observed with the i.v. applicable preparation only at a dosage of 500 mg/kg body weight, i.e. the bronchospastic side effect of the preparation according to the invention is 250 times less.

On account of the chemical composition and the pharmacological properties, the immunogloblin-G-containing fractions according to the invention are excellently suited for use in the treatment of primary and secondary immune defects, A-gammaglobulinemia or hypogammaglobulinemia, antibody deficiency syndrome, virus infections or bacterial infections as well as autoimmune or immune complex diseases.

What is claimed is:

1. A method of producing a therapeutically or prophylactically applicable immunoglobulin-G-containing fraction from human or animal plasma, which fraction is substantially free from incompatibility-reaction causing substances comprising the following steps:
   treating human or animal plasma with ethanol at a temperature of below 0° C., to obtain an immunoglobulin-G-containing precipitate,
   removing ethanol from said immunoglobulin-G-containing precipitate to obtain an immunoglobulin-G-containing fraction,
   treating said immunoglobulin-G-containing fraction with an immobilized enzyme selected from the group consisting of trypsin, chymotrypsin and pancreas protease at an elevated temperature of about 37° C. to obtain a treated fraction
   removing the immobilized enzyme,
   precipitating from said treated fraction a purified immunoglobulin substantially comprised of IgG by a protein precipitating agent,
   dissolving said precipitate to obtain a solution,
   sterile filtering said solution, and lyophilizing.

2. A method of producing an immunoglobulin-G-containing fraction as set forth in claim 1, wherein removal of ethanol from said immunoglobulin-G-containing precipitate is effected by dialysis.

3. A method of producing an immunoglobulin-G-containing fraction as set forth in claim 1, wherein removal of ethanol from said immunoglobulin-G-containing precipitate is effected by diafiltration.

4. A method of producing an immunoglobulin-G-containing fraction as set forth in claim 1, wherein removal of ethanol from said immunoglobulin-G-containing precipitate is effected by freeze-drying.

* * * * *